US012667283B2

(12) United States Patent
Gerhardt et al.

(10) Patent No.: US 12,667,283 B2
(45) Date of Patent: Jun. 30, 2026

(54) SENSOR UNIT, BODY FLUID MONITORING DEVICE AND METHOD FOR DETECTING AN ANALYTE

(71) Applicant: KONINKLIJKE PHILIPS N.V., Eindhoven (NL)

(72) Inventors: Lutz Christian Gerhardt, Eindhoven (NL); Ron Martinus Laurentius Van Lieshout, Geldrop (NL); Mark Thomas Johnson, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1314 days.

(21) Appl. No.: 17/292,800

(22) PCT Filed: Nov. 14, 2019

(86) PCT No.: PCT/EP2019/081338
§ 371 (c)(1),
(2) Date: May 11, 2021

(87) PCT Pub. No.: WO2020/099570
PCT Pub. Date: May 22, 2020

(65) Prior Publication Data
US 2021/0393173 A1      Dec. 23, 2021

(30) Foreign Application Priority Data
Nov. 14, 2018    (EP) ..................................... 18206129

(51) Int. Cl.
A61B 5/145       (2006.01)
A61B 5/00        (2006.01)
A61B 5/1468      (2006.01)

(52) U.S. Cl.
CPC ........ *A61B 5/14517* (2013.01); *A61B 5/1468* (2013.01); *A61B 5/6801* (2013.01); *A61B 2562/0295* (2013.01); *A61B 2562/046* (2013.01)

(58) Field of Classification Search
CPC . A61B 5/14517; A61B 5/1468; A61B 5/6801; A61B 2562/0295;
(Continued)

(56) References Cited

U.S. PATENT DOCUMENTS

| | | | |
|---|---|---|---|
| 6,511,854 B1 | 1/2003 | Asanov | |
| 9,274,082 B2 | 3/2016 | Sivan | |

(Continued)

FOREIGN PATENT DOCUMENTS

| | | |
|---|---|---|
| JP | 2001079548 A | 3/2001 |
| JP | 2007078488 A | 3/2007 |

(Continued)

OTHER PUBLICATIONS

International Search Report and Written Opinion, International Application No. PCT/EP2019/081338, Mailed on Dec. 11, 2019.
(Continued)

*Primary Examiner* — Tse W Chen
*Assistant Examiner* — Joseph A Tombers
(74) *Attorney, Agent, or Firm* — Brynne J. Corcoran

(57) ABSTRACT

Provided is a sensor unit (104) for detecting an analyte (128) in an aqueous medium. The sensor unit comprises a surface (124) for receiving the aqueous medium thereon. Capture species (126) immobilized on the surface reversibly bind the analyte. A detector (130) detects the analyte when the analyte is bound to the capture species. The sensor unit further comprises an electrolysis assembly (132). The electrolysis assembly comprises a plurality of spatially separated electrically conductive areas (134) on the surface, and a (Continued)

power supply (136) for supplying a voltage across at least two of the electrically conductive areas. The voltage is sufficient to electrolyse the aqueous medium received on the surface. Further provided is a body fluid monitoring device (101) comprising the sensor unit, and a method for detecting an analyte.

20 Claims, 7 Drawing Sheets

(58) Field of Classification Search
CPC ........ A61B 2562/046; A61B 2562/245; A61B 5/4266; G01N 33/54393
See application file for complete search history.

(56) References Cited

U.S. PATENT DOCUMENTS

| | | |
|---|---|---|
| 2005/0247559 A1 | 11/2005 | Frey et al. |
| 2009/0205974 A1 | 8/2009 | Sivan |
| 2009/0263891 A1* | 10/2009 | Gillies ............. G01N 33/54366 |
| | | 435/287.2 |
| 2013/0217003 A1 | 8/2013 | Hanko et al. |
| 2014/0191186 A1 | 7/2014 | Reed et al. |
| 2019/0029654 A1* | 1/2019 | Heikenfeld ........ A61B 5/14546 |

FOREIGN PATENT DOCUMENTS

| | | |
|---|---|---|
| WO | 9906835 A1 | 2/1999 |
| WO | 2016138087 A1 | 9/2016 |

OTHER PUBLICATIONS

Shin, S. et al., "Label-free and regenerative electrochemical microfluidic biosensors for continual monitoring of cell secretomes", Advanced Science, vol. 4, No. 5, May 2017.

Goode, J. et al., "Biosensor regeneration: a review of common techniques and outcomes", vol. 31, No. 23, Jun. 2015.

Geo, W. et al., "Fully integrated wearable sensor arrays for multiplexed in situ perspiration analysis", Article in Nature. Jan. 2016.

Zauner, D. et al., "Regenerative biosensor chips based on switchable mutants of avidin—A systematic study", Sensors and Actuators B 229 (2016) 646-654.

Toma, K. et al., "Regeneratable Surface Acoustic Wave (SAW) Immunosensor for Monitoring of Physiological Information", 2017 Eleventh International Conference on Sensing Technology (ICST).

Ortiz-Movilla, N. et al., "Hepatitis C Virus Replicates in Sweat Glands and Is Released into Sweat in Patients with Chronic Hepatitis C", Journal of Medical Virology 68, 529-536, 2002.

Millipore Sigma, "Antibody Basics", http://www.sigmaaldrich.com/technical-documents/articles/biology/antibody-basics.html, Accessed on May 4, 2021.

Mena-Bravo, A. et al., "Sweat: A sample with limited present applications and promising future in metabolomics", Journal of Pharmaceutical and Biomedical Analysis 90, (2014) 139-147.

Albert, Biomarkers and Heart Disease, J Clin Sleep Med. 2011, https://www.ncbi.nlm.nih.gov/pmc/articles/PMC3190417/.

Ravi Kant Upadhyay, Emerging Risk Biomarkers in Cardiovascular Diseases and Disorders, J Lipids, 2015, https://www.hindawi.com/journals/jl/2015/971453/.

Marques-Deak et al, Measurement of cytokines in sweat patches and plasma in healthy women: validation in a controlled study, J Immunol Methods. Aug. 2006, https://www.ncbi.nlm.nih.gov/pubmed/16942779.

Munje et al, A new paradigm in sweat based wearable diagnostics biosensors using Room Temperature Ionic Liquids (RTILs), Scientific Reports, vol. 7, Article No. 1950 (2017) https://www.nature.com/articles/s41598-017-02133-0.

Angela Mc Ardle, Brian Flatley, Stephen R. Pennington, Early biomarkers of joint damage in rheumatoid and psoriatic arthritis. Arthritis Res Ther. 2015; 17(1): 141. https://www.ncbi.nlm.nih.gov/pmc/articles/PMC4450469/.

Heba N Iskandar and Matthew A Ciorba, Biomarkers in Inflammatory Bowel Disease: Current Practices and Recent Advances. Transl Res. Apr. 2012; 159(4): 313-325. https://www.ncbi.nlm.nih.gov/pmc/articles/PMC3308116/.

Janeway CA Jr, Travers P, Walport M, et al. The structure of a typical antibody molecule. New York: Garland Science; 2001. https://www.ncbi.nlm.nih.gov/books/NBK27144/.

Harry W Schroeder, Jr, and Lisa Cavacini, Structure and Function of Immunoglobulins, J Allergy Clin Immunol. Feb. 2010; 125(2 0 2): S41-S52. https://www.ncbi.nlm.nih.gov/pmc/articles/PMC3670108/.

Elgert, Antibody structure and function (chapter 4) in: Immunology: Understanding the Immune System. http://www.wiley.com/legacy/products/subject/life/elgert/CH04.pdf, Accessed May 6, 2021.

Mohajeri et al., Preparation of a pH-sensitive pantoprazole-imprinted polymer and evaluation of its drug-binding and -releasing properties, Science China Chemistry, vol. 57, Issue 6, pp. 857-865, https://link.springer.com/article/10.1007/s11426-014-5091-1, Jun. 2014.

Optimize elution conditions for immunoaffinity purification. https://tools.thermofisher.com/content/sfs/brochures/TR0027-Elution-conditions.pdf, 2009.

Li et al, Electroporation on microchips: the harmful effects of pH changes and scaling down, Science Reports, 2015, https://www.nature.com/articles/srep17817#supplementary-information.

van Oss CJ, Good RJ, Chaudhury MK, Nature of the antigen-antibody interaction. Primary and secondary bonds: optimal conditions for association and dissociation. J Chromatogr. Apr. 11, 1986;376:111-9; https://www.ncbi.nlm.nih.gov/pubmed/3711190.

Medtronic: Low Battery Voltage Displayed at Device Interrogation, http://wwwp.medtronic.com/productperformance/document.html?id=450051, Feb. 2010.

Fakhar et al., Management of deep brain stimulator battery failure: battery estimators, charge density, and importance of clinical symptoms. PLoS One. 2013;8(3):e58665. https://www.ncbi.nlm.nih.gov/pubmed/23536810.

Mallela et al., Trends in cardiac pacemaker batteries. Indian Pacing Electrophysiol J. 2004, 4(4):201-12. https://www.ncbi.nlm.nih.gov/pubmed/16943934.

Eichmeier, Medizinische Elekronik, Springer: Sicherheit medizinischer Geraete, (1997); p. 178-179. http://www.springer.com/gp/book/9783642644320.

Islam, Electrophoretic Concentration and Electrical Lysis of Bacteria in a Microfluidic Device Using a Nanoporous Membrane, Micromachines 2017, 8(2), 45; http://www.mdpi.com/2072-666X/8/2/45.

Venge et al., Human Neutrophil Lipocalin as a Superior Diagnostic Means To Distinguish between Acute Bacterial and Viral Infections. Clin Vaccine Immunol. Sep. 2015;22(9):1025-32. https://www.ncbi.nlm.nih.gov/pubmed/26135974.

Z. Sonner, E. Wilder, J. Heikenfeld, G. Kasting, F. Beyette, D. Swaile, F. Sherman, J. Joyce, J. Hagen, N. Kelley- Loughnane, and R. Naik. The microfluidics of the eccrine sweat gland, including biomarker partitioning, transport, and biosensing implications. Biomicrofluidics 9, 031301 (2015).

K. Sato, W. H. Kang, K. Saga, and K. T. Sato, "Biology of sweat glands and their disorders. I. Normal sweat gland function," J. Am. Acad. Dermatol. 20, 537-563 (1989).

N. De Giovanni and N. Fucci, "The current status of sweat testing for drugs of abuse: A review," Curr. Med. Chem. 20, 645-561 (2013).

SCRAM continuous alcohol monitoring product, Alcohol Monitoring Systems, Inc., 2017.

Wescor Nanoduct Neonatal sweat analysis system, 2006, Wescor, Inc.

Bandodkar, A. J. et al. Epidermal tattoo potentiometric sodium sensors with wireless signal transduction for continuous non-invasive sweat monitoring. Biosens. Bioelectron. 54, 603-609 (2014).

Rose, D. P. et al. Adhesive RFID sensor patch for monitoring of sweat electrolytes. IEEE Trans. Biomed. Eng. 62, 1457-1465 (2015).

(56)  References Cited

OTHER PUBLICATIONS

T. Guinovart, G. Valdes-Ramirez, J. R. Windmiller, F. J. Andrade, and J. Wang, "Bandage-based wearable potentiometric sensor for monitoring wound pH," Electroanalysis 26, 1345-1353 (2014).
Bandodkar, A. J. & Wang, J. Trends Biotechnol. 32, 363-371 (2014).

* cited by examiner

124

140

138

124

140

138

SENSOR UNIT, BODY FLUID MONITORING DEVICE AND METHOD FOR DETECTING AN ANALYTE

This application is the U.S. National Phase application under 35 U.S.C. § 371 of International Application No. PCT/EP2019/081338, filed on 14 Nov. 2019, which claims the benefit of European Application Serial No. 18206129.1, filed 14 Nov. 2018. These applications are hereby incorporated by reference herein.

FIELD OF THE INVENTION

This invention relates to a sensor unit for detecting an analyte, and a body fluid monitoring device comprising the sensor unit. This invention further relates to a method for detecting an analyte.

BACKGROUND OF THE INVENTION

Non-invasive, semi-continuous and prolonged monitoring of biomarkers that indicate disease/health status and well-being is in demand for monitoring, for example, dehydration, stress, sleep, children's health and in perioperative monitoring.

Sweat, tear fluid and saliva may all be obtained non-invasively. Sweat is a particularly accessible biofluid, and is a rich source of information relating to the physiology and metabolism of a subject.

Some examples of clinical relevant components of sweat are $Na^+$, $Cl^-$ and/or $K^+$ to monitor dehydration, lactate as an early warning for inflammation (which is relevant to sepsis), glucose for diabetics and neonates, and cortisol in relation to sleep apnoea and stress monitoring.

The development of reliable sweat sensing has, however, been hampered by several issues, in spite of clinical work showing promising results as early as the 1940s and 1950s. To date the impactful application of sweat analysis has been limited mainly to cystic fibrosis diagnostics, and drugs and alcohol abuse testing.

As summarized by Mena-Bravo and de Castro in "Sweat: A sample with limited present applications and promising future in metabolomics" J. Pharm. Biomed. Anal. 90, 139-147 (2014), it has been found that the results from sweat sensing can be highly variable, and a correlation between values determined from blood and sweat samples appears to be lacking for various biomarkers. However, historical studies in this area of involved relatively crude sampling techniques, such as collecting large sweat volumes in bags or textiles. Deficiencies in such techniques may have been a contributing factor to this apparent lack of correlation.

Efforts have been made to address these issues by bringing wearable sensors into nearly immediate contact with sweat as it emerges from the skin. A very recent example is the wearable patch presented by Gao et al. in "Fully integrated wearable sensor arrays for multiplexed in situ perspiration analysis" Nature 529, 509-514 (2016). The patch includes a sensor array for measuring $Na^+$, $K^+$, glucose, lactate, and skin temperature. However, the focus of this study is on the development and the integration of the sensors themselves which, whilst evidently crucial, does not address issues relating to sweat sample collection. The latter is mostly done by placing a several $cm^2$ sized absorbent pad between the skin and the sensor. The assumption is that, providing ample sweat is produced (hence tests are always done on individuals that heavily exercise), the pad will absorb the sweat for analysis, and newly generated sweat will refill the pad and 'rinse away' the old sweat. It is, however, likely that the time-dependent response of the sensor does not directly reflect the actual level of biomarkers over time because of accumulation effects. The sample collection and presentation to the published sensors may not be well-controlled so that continuous reliable sensing over a long period of time is difficult. Such patches may also not be designed to handle the tiny amounts of sweat that are produced under normal conditions, i.e. in the order of nanoliters per minute per sweat gland.

Continuous monitoring of high-risk patients, such as those with serious chronic conditions, pre- or post-operative patients, and the elderly, using sweat biomarker monitoring devices can provide higher quality diagnostic information than regular biomarker spot checks as normally done by repeatedly drawing multiple blood samples. Such continuous monitoring may be in a hospital setting or elsewhere. Human sweat alone or as mixture with sebum lipids may be an easily accessible source for biomarker measurements in wearable on-skin devices. For instance, cholesterol is an important biomarker associated with elevated risk in development of cardiovascular diseases. Inflammatory markers or cytokines, such as interleukins (e.g. TNF-a, IL-6) play an important role in the immune response and detection or disease monitoring of joint damage in rheumatoid and psoriatic arthritis, and bowel disease.

Examples of biomarkers that can be detected in eccrine/apocrine sweat using suitable capture species (antibodies, aptamers, molecular imprint polymers, etc.) are: small molecules such as urea, creatinine, cholesterol, triglycerides, steroid hormones (cortisol), glucose, melatonin; peptides and proteins incl. cytokines such as IL-1alpha, IL-1beta, IL-6, TNF alpha, IL-8 and TGF-beta IL-6, Cysteine proteinases, DNAse I, lysozyme, Zn-$\alpha$2-glycoprotein, cysteine-rich secretory protein-3 and dermcidin; and large biomarkers such as the Hepatitis C virus.

However, improvements are required to existing devices for continuous or intermittent monitoring. In wearable or portable devices for monitoring biofluid samples, e.g. sweat, saliva, tear fluid, the detection of biomarkers or analytes in the biofluid of interest tends to require the device to include a sensor unit having a surface on which capture species are immobilized, which capture species bind the biomarker. Typically, the capture species are antibodies and the analyte is a corresponding antigen. However, the surface may become saturated with analytes, which prevents further analyte detection. This problem may render such a device unsuitable for long-term monitoring, as the sensor unit will have limited sensing lifetime and performance.

WO 99/06835 A1 discloses a regenerable biosensor using total internal reflection fluorescence with electrochemical control.

US 2013/217003 A1 discloses a method for determining an analyte content of a liquid sample by means of a bioanalyzer.

WO 2016/138087 A1 discloses a dynamic sweat sensor management system.

US 2005/247559 A1 discloses a biosensor array and a method for operating the biosensor array.

SUMMARY OF THE INVENTION

The invention is defined by the claims.

According to an aspect there is provided a sensor unit for detecting an analyte in an aqueous medium, the sensor unit comprising: a surface for receiving the aqueous medium thereon; capture species for reversibly binding the analyte, the capture species being immobilized on the surface; a detector for detecting, determining or assessing analyte bound to the capture species; and an electrolysis assembly comprising: at least three spatially separated electrically conductive areas on, or at least proximal to, the surface; and a power supply configured to implement: a first setting in which a voltage sufficient to electrolyse the aqueous medium received on the surface is supplied across a first pairwise combination of the at least three conductive areas; and a second setting in which a voltage sufficient to electrolyse the aqueous medium received on the surface is supplied across a second pairwise combination of the at least three conductive areas, the second pairwise combination being different from the first pairwise combination.

The detection principle of conventional sensor units for detecting an analyte relies on capture species immobilized on a surface, i.e. a sensor surface. The capture species may be selected to bind a certain analyte. For example, antibodies may be immobilized on the surface, which antibodies capture a particular antigen; the antigen being the analyte of interest. Thus, when a sample contacts the surface, the capture species may bind the analyte present in the sample. When the analyte is bound to the surface via the capture species, various properties, e.g. optical and mechanical characteristics, of the surface are altered with respect to the analyte-free surface.

The reversible nature of the binding of the analyte to the capture species means that the analyte may in principle be liberated from the capture species, thereby to regenerate the sensor surface for further analyte detection. For example, the conditions in the vicinity of the sensor surface may be modified by, for example, rinsing the surface with a relatively low pH (or a relatively high pH) solution so as to disrupt, e.g. denature, the capture species-analyte complex. Alternatively, the surface may be contacted with a solution of a compound that mimics the capture species-analyte binding site, and to which the analyte preferentially binds. Further, an agent may be used which induces an allosteric change which causes release of the analyte. The disadvantage of these approaches is that they rely on a reagent, e.g. elution buffer, for effecting the regeneration. Either the sensor unit would have to be manually refreshed periodically, or else would require storage vessels containing the reagent. It would be desirable to remove, or at least to minimize, the requirement for such reagents to regenerate the surface.

The present invention is based on the realization that electrolysis of the aqueous medium may be employed to regenerate the surface (water is the main component of body fluids), such as to remove or minimize the requirement for reagents to effect regeneration. To this end, the sensor unit comprises an electrolysis assembly for electrolysing the aqueous medium, i.e. the sample, which contains the analyte. A voltage, e.g. a voltage profile, is supplied across pairwise combinations of a plurality of spatially separated conductive areas on the surface; the respective conductive areas of each pairwise combination thus becoming an anode and a cathode. The voltage is sufficient to electrolyse the aqueous medium, which results in hydrogen ions being produced at the anode, and hydroxyl ions being produced at the cathode. The pH local to the anode may thus be lowered, and the pH local to the cathode may be increased. These localized changes to the pH may result in disruption, e.g. denaturation, of the capture species-analyte complex, such as to regenerate at least part of the surface.

The voltage employed in the first setting may be the same as or different to the (further) voltage employed in the second setting. When the respective voltages are different from each other, they may differ in magnitude and/or polarity.

The respective pairwise combinations may, for example, be different from each other in terms of both the spacing between the conductive areas and the arrangement of voltage polarity applied to the (alternating) conductive areas.

The capability of the power supply to implement the first and second settings may be of particular assistance when, for example, the electrically conductive areas cannot be made of optically transmissive materials. When a detection principle is employed which requires optical interrogation of the surface, such as surface plasmon resonance, electrically conductive areas which are insufficiently optically transmissive may mean that only regions therebetween may be used for analyte sensing. However, capture species located between the electrically conductive areas may be more likely to coincide with a pH neutral zone during regeneration if only a single setting were employed; little or no regeneration occurring in such a pH neutral zone. The first and second settings may mean that a greater proportion of the capture species located between the conductive areas may be regenerated by applying voltage profiles over different pairwise (consecutive or spatially separated) conductive areas.

The voltage may be different in the first and second configurations. For example, the voltage may be higher or linearly increasing in the second setting than in the first setting. Alternatively or additionally, the second pairwise combination of conductive areas may be spaced further apart on the surface than the first pairwise combination of conductive areas. Such measures may assist to increase the degree of electrolytic regeneration of the surface.

The conductive areas may be arranged relative to each other in an interdigitated configuration, e.g. in a planar interdigitated configuration. The interdigitated configuration may assist to provide the voltage over a relatively large area, e.g. in the order of several mm$^2$ to cm$^2$, whilst providing localities on the surface in which the local pH changes resulting from water electrolysis drive regeneration. A similar effect may be achieved using, for instance, electrically conductive areas arranged as a plurality of concentric ring-like portions.

The plurality of spatially separated electrically conductive areas may comprise an array of conductive areas in which the spacing between adjacent conductive areas alternates between a larger and a smaller separation, wherein the power supply may be configured to supply the voltage across adjacent conductive areas spaced by the larger separation, the adjacent conductive areas spaced by the smaller separation being of the same polarity as each other. Such an arrangement may assist to reduce the area on the surface in which electrolytic regeneration does not occur. Accordingly, the degree of electrolytic regeneration of the surface may be enhanced.

The plurality of spatially separated electrically conductive areas may comprise a grid of electrically conductive strips, the power supply being configured to implement: a first mode in which the voltage (profile) is supplied across parallel strips extending in a first direction; and a second mode in which the voltage is supplied across parallel strips extending in a second direction, the second direction being different from the first direction. The power supply may, for instance, be configured to implement the first and second modes sequentially. More complete regeneration of the surface may thus be achieved.

The power supply may be configured to switch the polarity of the voltage across the at least two electrically conductive areas. Certain antibody-antigen complexes, for instance, may be denatured only at an optimum acidic or alkaline pH, and are otherwise robust to large pH variations. For this reason, the power supply may be configured to switch the polarity of the voltage across the respective electrically conductive areas or superimpose a larger AC voltage to a DC voltage to switch the polarity of the electrodes and direction of the electric field. This polarity switch may result in regeneration of capture species located proximal to both of the respective conductive areas.

The detector may comprise a transducer. The detector may, for example, comprise at least one of a quartz crystal resonator detector and a surface plasmon detector. Alternatively or additionally, the detector may comprise a 'frustrated' total internal reflection detector. Such detectors may enable label-free detection of the analyte. Label-free detection is particularly advantageous because the detection does not rely on the use of reagents.

The transducer may be arranged to transmit and/or receive electrical signals via at least some of the plurality of spatially separated electrically conductive areas. By employing the conductive areas for both detection and regeneration, the design of the surface may be advantageously simplified.

The conductive areas may comprise an optically transmissive material, such as an optically transparent material for enabling optical detection of the analyte bound to the capture species.

The sensor unit may comprise a controller configured to trigger the electrolysis assembly to electrolyse the aqueous medium in response to a trigger signal. Triggering electrolytic regeneration of the surface in this manner may be advantageous in terms of enabling long-term automatic monitoring of the subject. When the power supply comprises a cell or battery, such control over the electrolysis assembly may assist to conserve cell- or battery-life.

The controller may comprise a clock module configured to send a clock signal to the controller at predetermined intervals, the trigger signal comprising the clock signal.

Alternatively or additionally, the controller may comprise a sensor signal variation module configured to generate a variation signal in response to a signal received from the detector, the trigger signal comprising the variation signal. The signal variation module may, for example, be configured to generate the variation signal in response to saturation of the detector. By triggering electrolytic regeneration when the detector signal is indicative of deterioration or saturation, the sensor unit may provide an automatic response by regenerating the surface, such as to restore sensing performance.

The sensor unit may comprise a further sensor for monitoring a body parameter, the further sensor being configured to generate an event signal in response to a change in the body parameter, wherein the trigger signal comprises the event signal. The regeneration of the surface may thus be triggered by a physiological event, such as a rise or drop in heart rate/respiration rate, a rise in core body temperature or an abnormal electrocardiogram. The sensor unit may therefore be prepared for analyte sensing when the physiological condition of the subject indicates that such analyte sensing would be of diagnostic use.

According to another aspect there is provided a body fluid monitoring device for detecting an analyte in an aqueous medium produced by the body, the device comprising: the sensor unit as defined above; and a fluid collection assembly for supplying the aqueous medium to the surface of the sensor unit. The device may be, for example, a sweat monitoring device and the aqueous medium may thus comprise sweat.

According to a further aspect, there is provided a method for detecting an analyte in an aqueous medium, the method comprising: providing capture species immobilized on a surface; receiving the aqueous medium on the surface such that the analyte binds to the capture species; detecting, determining or assessing the bound analyte; and releasing the detected analyte from the capture species by electrolysing the aqueous medium received on the surface, wherein the electrolysing comprises supplying a voltage sufficient to electrolyse the aqueous medium across a first pairwise combination of at least three conductive areas, and supplying a voltage sufficient to electrolyse the aqueous medium across a second pairwise combination of the at least three conductive areas, the second pairwise combination being different from the first pairwise combination.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figures 1, 2:
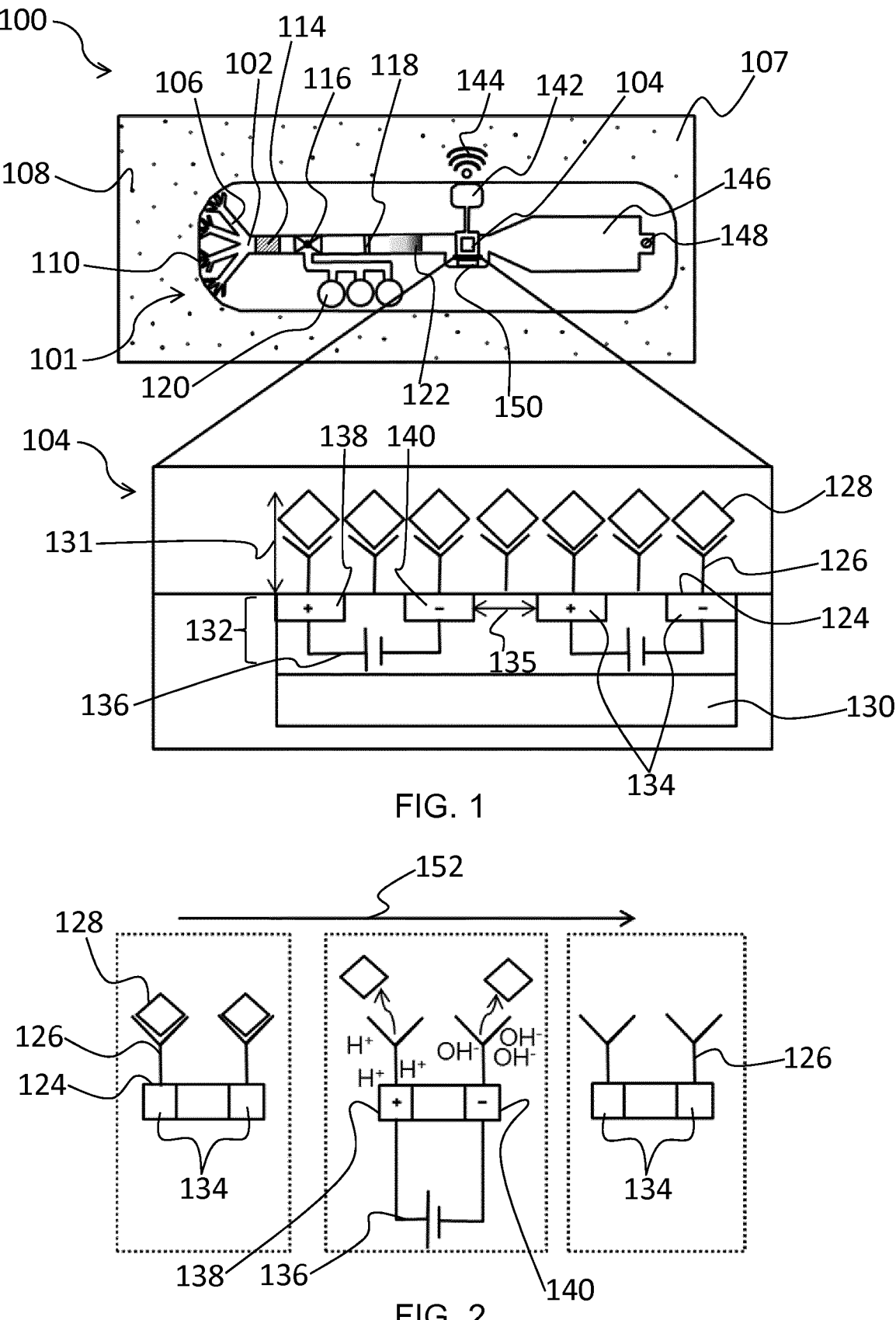
FIG. 1 schematically depicts a body fluid monitoring device according to an embodiment, with an inset showing a magnified view of the sensor unit included in the device.
FIG. 2 schematically depicts regeneration of a capture surface of a sensor unit according to an embodiment.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

Provided is a sensor unit for detecting an analyte in an aqueous medium. The sensor unit comprises a surface for receiving the aqueous medium thereon. Capture species immobilized on the surface reversibly bind the analyte. A detector detects the analyte when the analyte is bound to the capture species. The sensor unit further comprises an electrolysis assembly. The electrolysis assembly comprises a plurality of spatially separated electrically conductive areas on the sensor surface, and a power supply for supplying a voltage across at least two of the electrically conductive areas. The voltage is sufficient to electrolyse the aqueous medium received on the surface.

The detection principle of conventional sensor units for detecting an analyte relies on capture species immobilized on a surface. The capture species may be selected to bind a certain analyte. For example, antibodies may be immobilized on the surface, which antibodies capture a particular antigen; the antigen being the analyte of interest. Thus, when a sample contacts the surface, the capture species may bind the analyte present in the sample. When the analyte is bound to the surface via the capture species, various properties, e.g. optical and mechanical characteristics, of the surface are altered with respect to the analyte-free surface. This means that the bound analyte may be detected, determined or assessed using a suitable detector. The detection process may include monitoring a change in the surface resulting from binding of the analyte to the capture species; the change being related, i.e. proportional, to the concentration of the analyte.

To ensure accurate detection within the sensitive linear regime of the analyte dose response curve, the capture species may need to exhibit a relatively high association rate, i.e. a relatively high number of binding events per unit time, and a low dissociation rate, i.e. a relatively low number of decay events per unit time. The surface may, however, become saturated with the analyte so that there are no available capture species to which further analyte may bind. This saturation problem may prevent the sensor unit from being used for intermittent or continuous long-term monitoring, because of the associated restricted sensing lifetime and performance. To enable long-term monitoring in which the surface is prevented from becoming saturated and the analyte response curve is maintained in the linear region, the surface may require regular cleaning and regeneration.

The reversible nature of the binding of the analyte to the capture species means that the analyte may be liberated from the capture species, thereby to regenerate the surface for further analyte detection. For example, the conditions in the vicinity of the sensor surface may be modified by, for example, rinsing the surface with a relatively low pH (or a relatively high pH) solution so as to disrupt, e.g. denature, the capture species-analyte complex. Alternatively, the sensor surface may be contacted with a solution of a compound that mimics the capture species-analyte binding site, and to which the analyte preferentially binds. Further, an agent may be used which induces an allosteric change which causes release of the analyte. The disadvantage of these approaches is that they rely on a reagent, e.g. elution buffer, for effecting the regeneration. Either the sensor unit would have to be manually refreshed periodically, or else would require storage vessels containing the reagent. It would be desirable to remove, or at least to minimize, the requirement for such reagents to regenerate the surface.

The present invention is based on the realization that water electrolysis may be employed to regenerate the surface, such as to remove or minimize the requirement for reagents to effect regeneration. To this end, the sensor unit comprises an electrolysis assembly for electrolysing the aqueous medium, i.e. the sample, which contains the analyte. A voltage is supplied across at least two of a plurality of spatially separated conductive areas on the surface; the at least two conductive areas thus becoming an anode and a cathode. The voltage is sufficient to electrolyse the water, which results in hydrogen ions being produced at the anode (Equation 1), and hydroxyl ions being produced at the cathode (Equation 2). The pH local to the anode may thus be lowered, and the pH local to the cathode may be increased. These localized changes to the pH may result in disruption, e.g. denaturation, of the capture species-analyte complex, such as to regenerate at least part of the surface.

$$2H_2O(l) \rightarrow O_2(g) + 4H+(aq) + 4e^- \qquad \text{(Equation 1)}$$

$$4H_2O(l) + 4e^- \rightarrow 2H_2(g) + 4OH^-(aq) \qquad \text{(Equation 2)}$$

FIG. 1 schematically depicts an in situ configuration 100 of a body fluid monitoring device 101 according to its intended use. The device 101 shown in FIG. 1 is a sweat monitoring device, but this is for explanatory purposes only; the principles explained herein being applicable to monitoring bodily fluids other than sweat, e.g. saliva, tear fluid, etc.

The device 101 comprises a fluid collection assembly/stage 102 which supplies an aqueous medium, i.e. sample, to the sensor unit 104. The fluid collection assembly/stage 102 may comprise a microfluidic system comprising interconnected fluid channels 106 which convey the sample to the sensor unit 104. In this manner, the sample may be regarded as indirectly accessing the sensor unit 104, via the fluid collection assembly 102.

In alternative non-limiting examples, the sensor unit 104 may be in direct contact with the body, i.e. with no fluid collection assembly being required to transport the sample to the sensor unit 104. The sensor unit 104 may thus be directly exposed to the sample biofluid, e.g. sweat. Such a device 101 may thus be regarded as an 'open' sensor system. Although the lifetime of such open system may be limited, such an open system might have the advantage that it reduces or even prevents biofouling, i.e. since fewer or no microfluidic channels may be included in the open sensor system. A low pH, e.g. a local acidic pH provided by water electrolysis, may, for instance, prevent bacterial growth on such a system.

In the example shown in FIG. 1, the device 101 comprises a patch on the skin 107. The aqueous medium is included in the sweat excreted from the pores 108 of the skin 107 to which the device 101 is attached. The device 101 may be attached, e.g. adhered, to the skin 107 in any suitable manner, such as using a suitable biocompatible adhesive or fixation straps.

The fluid collection assembly 102 shown in FIG. 1 comprises sample uptake channels 106 which receive sweat from the skin 107. The sample uptake channels 106 may be coupled to the skin 107 via the skin attachment members 110. The samples from the respective sample uptake channels 106 are combined to form the sample collection assembly/stage 102, before being pretreated at the sample pretreatment stage 114. The pretreatment may, for example, comprise filtering of the sample.

A valve 116, in combination with a flow sensor 118, may control the flow of the sample in the device 101. The device 101 may include a reagent supply 120 for supplying one or more stored reagents to the sensor unit 104, although the requirement to use such a reagent for sensor regeneration may be minimized or removed, as previously explained. The fluid collection assembly 102 may further include an analyte upconcentration stage 122, due to the potentially minute, e.g. nanomolar, quantities of biomarkers, i.e. analytes, present in sweat samples.

When the sample reaches the sensor unit 104, the sample contacts the surface 124 of the sensor unit 104, which is shown in greater detail in the inset of FIG. 1. Capture species 126 are immobilized on the surface 124. The surface 124 may thus be termed a 'capture surface' due to the capability of the capture species 126 immobilized thereon to reversibly bind the analyte 128 contained in the sample. The inset of FIG. 1 schematically depicts each of the capture species 126 binding a respective analyte 128.

A monolayer of capture species 126 on the surface 124 is depicted in FIG. 1, which may assist the detection, e.g. optical detection, of the bound analyte 128. This, however, is not intended to be limiting, and any number of layers of capture species 126 may be provided on the surface 124, providing the detector 130 is capable of detecting the analyte 128 bound to the capture species 126.

With the analyte 128 bound to the capture species 126, the distance 131 from the surface 124 to the extremity of the analyte 128 furthest from the surface 124 may be, for instance, 5 nm to 50 nm, such as about 20 nm, depending on the size characteristics of the capture species 126 and the analyte 128.

The capture species 126 may be selected according to the particular analyte 128 which the sensor unit 104 is intended to sense. Relevant analytes 128 include, for instance, small-molecule compounds, e.g. having a molecular weight less than 900 g/mol, such as urea, creatinine, cholesterol, triglycerides, steroid hormones, e.g. cortisol, glucose and melatonin.

Other small-molecule compounds, such as drug molecules may also be captured with suitable capture species 126. However, certain immunoassay methods, such as the sandwich immunoassay method, may be precluded for such small-molecule compounds, since such small-molecules may only have a single binding site. Moreover, when used in label-free detection, small-molecules may only induce a small signal change, which may mean an undesirably high detection limit for the device 101.

The capture species 126 may be selected to bind other molecule types, such as peptides and proteins. For a protein, the capture species 126 may reversibly bind via an epitope of the protein for which the capture species 126 includes a suitable binding site. The capture species 126 may, for example, be selected to bind cytokines such as IL-1alpha, IL-1beta, IL-6, TNF-alpha, IL-8 and TGF-beta IL-6, Cysteine proteinases, DNAse I, lysozyme, Zn-α2-glycoprotein, cysteine-rich secretory protein-3 and dermcidin. Protein binding may, for instance, enable binding and detection of relatively large biomarkers, such as viruses, to the surface 124. This is particularly relevant to sweat sensing because certain viruses, such as the hepatitis C virus, may replicate in sweat glands and be released in sweat.

Analytes 128 in general, and in particular relatively large analytes 128, e.g. having a molecular weight greater than 900 g/mol, may be detected by measuring a parameter associated with binding of the analyte 128 to the capture species 126.

In principle any molecule, or macromolecule, having a specific three-dimensional structure, including, for instance, lipids, can be bound to an appropriately selected capture species 126.

In a non-limiting example, the analyte 128 may be an antigen and the capture species 126 may include an antibody. Immunoglobulin (IgG) may, for instance, be a suitable antibody for immobilizing on the surface 124. IgG is the most common type of antibody in the human circulation system. Antibodies may be used to capture a wide range of molecules. The antibody structure generally comprises a constant domain (Fc) and an antigen binding domain (Fab), but other forms containing, for instance, only the Fab part, or a portion of the Fab part, may be used. The antigen may include, for example, proteins and polysaccharides.

As is well-known per se, antibodies comprise proteins that are produced to fight foreign intruding species, such as viruses. A so-called 'lock and key' interaction selectively binds the antigen to the antibody. The strength of the binding between the antibody and the antigen is termed the 'affinity'. The affinity corresponds to the sum of the attractive and repulsive forces between the antigen and the antibody in the relevant binding site of the antibody. The attractive force is determined, at least in part, by the number of attractive antigen-antibody interactions at the binding site.

Non-covalent interactions, such as hydrogen bonds, electrostatic interactions, van der Waals forces and hydrophobic interactions, between the antibody and the antigen may mean that the binding of the antigen to the antibody is reversible. Accordingly, adjustment to the charge and/or configuration of the antibody may result in the number of attractive antigen-antibody interactions being reduced. Moreover, the sum of the repulsive forces may, for instance, be increased, e.g. due to net charge changes of the antibody and the antigen respectively. The 'fit' between the antigen and the antibody may therefore be disrupted by making such an adjustment, such that the antigen is released from the antibody.

The capture species 126 may, for instance, include aptamers, which are oligonucleotide or peptide molecules that bind to a specific target molecule. As in the case of antibodies they rely on their three-dimensional configuration in order to attain the requisite affinity for the analyte 128.

In other examples, the capture species 126 may include molecular imprint polymers, which are polymers that are imprinted with an antigen, or part of an antigen. Such materials may comprise a cavity that has a three-dimensional configuration which complements the three-dimensional shape of the antigen, so as to attain the requisite 'lock and key' structure. Molecular imprint polymers may change their structure due to pH changes. One example is a pH sensitive pantoprazole-imprinted polymer, which is known to bind or release a drug according to the pH.

The capture species 126 may be immobilized on the surface 124 in any suitable manner. In a non-limiting example, a suitable mercaptan linker may be used to tether the capture species 126 to a gold surface 124; the linker being grafted to the surface 124 via a sulphur-gold interaction and the capture species 126 being grafted, e.g. covalently bonded, to the linker. Numerous alternative means of immobilizing the capture species 126 on the surface 124 will be immediately apparent to the skilled person.

The sensor unit 104 comprises a detector 130 for detecting the analyte 128 when the analyte 128 is bound to the capture species 126. The detector 130 may, for instance, be included in, e.g. integrated into, a body comprising the surface 124.

Any suitable detector 130 may be used for detecting the bound analyte 128. In an embodiment, the detector 130 comprises a transducer. The transducer may, for example, include a piezoelectric material between a pair of conductive areas. The detector 130 may thus comprise an acoustic microsensor for detecting the subtle changes to the surface 124 when the analyte 128 is bound thereto via the capture species 126.

In a non-limiting example, the detector 130 may comprise at least one of a quartz crystal resonator detector, a surface plasmon detector and a 'frustrated' total internal reflection detector. Such detectors 130 may enable label-free detection of the analyte 128. Label-free detection is particularly advantageous because the detection does not rely on the use of labelling and/or secondary binding and a simple sample elution process may be enabled through the supply of fresh aqueous medium to the sensor unit 104. Sweat itself may be used as an eluent to remove or transport away unbound analytes from the surface by running sweat through the system.

In the case of a quartz crystal detector 130, the surface 124 may comprise electrodes, e.g. gold electrodes. The electrodes and the quartz constitute a transducer arrangement. Mass variation per unit area of the surface 124 may be determined by measuring any changes in the resonance frequency of the quartz crystal. Such changes may correspond to the analyte 128 binding to, or being released from, the capture species 126 immobilized on the surface 124.

An electrolysis assembly 132 is included in the sensor unit 104. The electrolysis assembly 132 comprises a plurality of spatially separated electrically conductive areas 134 on the surface 124. The electrically conductive areas 134 are spaced by a spacing 135, as shown in the inset of FIG. 1. The spacing 135 may be, for instance, in the range of 0.1 mm to 3 mm, such as about 1.5 mm.

In an embodiment, the transducer of the detector 130 may be arranged to transmit and/or receive electrical signals via at least some of the electrically conductive areas 134. In this manner, the electrically conductive areas 134 may be employed in a sensing mode and in a regeneration mode. By employing the conductive areas 134 for both detection and regeneration, the design of the surface 124 may be advantageously simplified.

For example, when the detector 130 comprises a quartz crystal detector, the electrically conductive areas 134 may be employed as electrodes in the sensing mode to measure the binding, e.g. binding kinetics, of the analyte 128 to the capture species 126. In the regeneration mode, the electrically conductive areas 134 may be employed as stimulation electrodes 138, 140 for electrolysing the aqueous medium on the surface 124.

In an embodiment, the electrically conductive areas 134 may be formed of an optically transmissive material, e.g. a transparent conductive material, such as indium tin oxide or poly(3,4-ethylenedioxythiophene):poly(4-styrenesulfonate). Such optically transmissive conductive materials may maximise the available sensing area and enable use of optical detectors 130 for label-free detection of regenerated capture species 126.

The surface 124 patterned with the electrically conductive areas 134 may be manufactured using any suitable technique. For example, suitable patterning methodologies are known from the fields of printed electronics, thin film technology, laser ablation, etc. Non-optically transmissive materials may alternatively or additionally be employed for the electrically conductive areas 134. Optical interrogation of the capture species 126 may be assisted when the conductive areas 134 are not optically transmissive by arranging the conductive areas 134 between areas of the surface 124 on which the capture species 126 are immobilized.

The electrolysis assembly 132 further comprises a power supply 136 for supplying a voltage across at least two of the electrically conductive areas 134; the latter thus constituting an anode 138 and a cathode 140. The voltage may be a D.C. voltage sufficient to electrolyse the water included in the sample received on the surface 124. Regeneration of the surface 124 using the electrolysis assembly 132 will be described in greater detail with reference to FIG. 2.

The power supply 136 shown in FIG. 1 comprises a cell or a battery, which may facilitate application of the sensor unit 104 in a wearable or portable device 101. Alternatively or additionally, the power supply 136 may comprise a voltage signal generator and/or suitable components, e.g. a transformer, for connecting the sensor unit 104 to a mains source of electricity. The mains may thus be used to charge the cells or batteries included in the power supply 136, and/or may be used in combination with a transformer to supply the electrodes 138, 140 with the requisite D.C. voltage.

The device 101 shown in FIG. 1 includes a controller 142 comprising control electronics, e.g. including a multiplexer, for controlling the sensor unit 104. At least some components of the power supply 136 may, for instance, be included in the controller 142.

The controller 142 may further include, for example, a communication module 144 for transmitting data obtained by the sensor unit 104 to a remote monitoring workstation (not shown). The communication module 144 may alternatively or additionally receive control signals input by a user on the remote monitoring workstation. In a non-limiting example, the communication module 144 may transmit and receive wirelessly to and from a tablet or mobile device loaded with suitable software for displaying or logging the data, and controlling the device 101.

A reference sensor 150 may, for example, be additionally included in the device 101. Downstream of the sensor unit 104, the device 101 shown in the FIG. 1 comprises a fluid transport system 146, which may assist in transporting the sample through the device 101. A vent 148 may be provided to permit any air, or other gases, e.g. the gases generated during electrolysis, present in the device 101 to be vented.

The (optional) reference sensor 150 and the fluid transport system 146, e.g. a microfluidic fluid transport system, are components which are well-known per se in the field of microfluidic biochemical sensors, and will not be further described herein for the sake of brevity only.

FIG. 2 schematically depicts regeneration of the surface 124. The surface 124 may become saturated when all of the capture species 126 are complexed to the analyte 128. This saturation is depicted in the far left hand pane of FIG. 2. The process of regenerating the surface 124 is depicted from left to right in FIG. 2, in the direction of the arrow 152. Electrically conductive areas 134 are provided on the surface 124, which conductive areas 134 constitute electrodes 138, 140 when a power supply 136 supplies a voltage across the conductive areas 134. This D.C. voltage is sufficient to electrolyse the water included in the aqueous medium of the sample when the sample contacts the surface 124.

In the case of a sweat sample, the aqueous medium may correspond to a dilute sodium chloride solution. A physiological sodium chloride concentration may be about 50 mmol/l in sweat (cf. 140 mmol/l in plasma). A typical sodium chloride concentration used in buffers is 0.9 wt. %. Electrolysis of such a dilute sodium chloride solution may approximate the electrolysis of water:oxygen gas being generated at the anode 138 (Equation 1) and hydrogen gas being generated at the cathode 140 (Equation 2). Electrolysis of more concentration sodium chloride solutions may result in chlorine gas being generated at the anode 138, as is well-known per se. Some of the formed gases can be re-absorbed or eliminated from the system using a vent 148. Oxygen gas is normally not generated when another donor ion is present ($Na^+$, $Cl^-$) or the sodium chloride concentration is high. Hydrogen gas will be absorbed by the sweat or converted to nanobubbles. As formed gas bubbles may be reabsorbed or too small to interfere with any microfluidic flow, they may not interfere with the working of the sensor (especially since electrolysis is used to regenerate the sensor)—i.e. the biomarker measurement may occur a period of time after generation of the small amount of gas produced during electrolysis is reabsorbed/dissolved in the aqueous medium (sweat).

According to Nernst, water electrolysis is effected at voltages greater than about 1.23 V under standard conditions, i.e. standard temperature (273.15 K) and standard pressure (100 kPa, 1 bar). In an embodiment, the voltage across the electrodes 138, 140 may be, for instance, in the range of 3 to 4.5 V.

As shown in the centre pane of FIG. 2, water electrolysis may result in a transient hydrogen ion (H$^+$) and hydroxyl (OH$^-$) ion concentration gradient forming between the anode 138 and cathode 140. The localized acidic zone proximal to the anode 138 may result in the analyte 128 being liberated from the capture species 126 in the acidic zone. Alternatively or additionally, the localized alkaline zone proximal to the cathode 140 may result in the analyte 128 being liberated from the capture species 126 in the alkaline zone.

Whether the binding between the capture species 126 and the analyte 128 is disrupted by the more acidic and/or the more alkaline pH resulting from water electrolysis may depend, for instance, on the nature of the binding site. The preferred pH for denaturation of an antibody-antigen complex may be in the acidic range, e.g. in the range of pH 2 to 3, although denaturation may also be effected under alkaline conditions. The local pH change may, for example, drive conformational change in the capture species 126. For example, when the capture species 126 comprise antibodies, the local change in pH may trigger unfolding of the secondary or tertiary structure of the antibody proteins.

It has been shown that, for example, localized shifts, e.g. down to pH 3 and up to pH 12, which are typical pH values for elution buffers, may be achieved using voltage pulses (12-120 V, pulse duration 0.1-1 ms, 5-20 pulses) generating an electric field in the order of $10^5$ V/m. When applying this principle in a sensor unit 104 for positioning on or inside the body, the electrochemical conditions may be selected to ensure safe operation, even when the sensor unit 104 is located, for example, inside the mouth.

The energy required to regenerate the surface 124 at pH 3 may be calculated using Faraday's law of electrolysis: Equation 3.

$$n = \frac{I \cdot t}{F} \cdot \frac{1}{z} = \frac{Q}{F \cdot z} \qquad \text{(Equation 3)}$$

where n is the number of moles of water altered at an electrode during electrolysis; F is the Faraday constant: 96485 C/mol; Q is the total electric charge in Coulombs (C) passed through the water, I is the current, t is the time that the constant current is applied; z is the number of electrons transferred per ion (for O$_2$, z=4).

The volume of the sensor unit 104 may be, for example, $10^{-2}$ mm$^3$ (10 mm×10 mm×$10^{-4}$ mm).

For a pH of 3, the concentration of hydrogen ions is 0.001 mol/L or 1 nmol/mm$^3$. For the $10^{-2}$ mm$^3$ volume of the sensor unit 104, the required number of moles of hydrogen ions is 0.01 nmol to attain a pH of 3. Using Equation 1

(electrolysis results in a 1:4 molar ratio of oxygen to hydrogen), 0.0025 nmol of O$_2$ is generated per 0.01 nmol of hydrogen ions, i.e. n=0.0025 nmol.

Using Equation 3, Q=n·F·z=0.0025 nmol×96485 C/mol× 4≈1 μC is needed to obtain pH 3 in a sensor capture unit volume of $10^{-2}$ mm$^3$.

1 μC may be provided using, for example, a current of 1 μA for 1 s or a current of 10 μA for 0.1 s.

$$\text{Power=Voltage×Current=3 V×10 μA=30 μW.}$$

$$\text{Energy=Power×Time=30 μW×0.1 s=3 μJ.}$$

Thus, the electrical power requirements (driving potential: 3V, current: 0.1-10 μA, current density≈0.02-0.2 μA/mm$^2$, field strength≈$10^3$ V/m) for electrolytic regeneration of the sensor unit 104 on or inside the body may be easily met and may conform to safety requirements of active implantable medical devices in accordance with EN45502-1 and EN 60601-1. The device 101 and sensor unit 104 may therefore be safe to use in various monitoring applications on or inside the body. For example, it may be desirable to place the sensor unit 104 under the skin for facile access to interstitial fluids. It is noted in this respect that adverse biological effects are considered highly unlikely from a medical device safety perspective for such an implantable device 101 or sensor unit 104.

A D.C. voltage of, for example, 3 V may be safe to use on or inside the body. Deep brain stimulation implants and pacemakers are typically driven by batteries using voltages of a few volts. According to EN 60601-1 and EN45502-1, active medical devices in direct contact with the human heart should have a patient leakage current of less than 10 μA. For instance for pacemakers, D.C. leakage currents to the surrounding tissue may be required not to exceed 100 nA to prevent excessive electrolytic effects.

Currents of, for example, 0.1-10 μA may be used to regenerate the surface 124 for between 10 s and 0.1 s, thereby to obtain the target charge Q of 1 μC necessary for a pH of 3 in a $10^{-2}$ mm$^3$ volume, as calculated above. The resultant current density may thus be less than 0.2 μA/mm$^2$, and therefore smaller than the critical value of 0.75 μA/mm$^2$ stated in EN45502-1.

The critical electric field strength E to induce cell lysis may be in the order of $10^5$ V/m. Assuming an electrode spacing 135 of 1.5 mm, and a voltage of 3 V, which may be sufficient for water electrolysis, the resultant field strength may be 2000 V/m, which is two orders of magnitude lower than the critical field strength for cell lysis.

To reduce the risk of local build-up of an undesirably high analyte 128 concentration during regeneration of the surface 124, a gradual change in pH may be effected by gradually increasing the voltage. In alternative examples, the voltage may be applied in relatively short pulses or bursts, which may be preferable for inducing the localized pH changes for surface 124 regeneration, providing the pulses may be implemented safely.

Once the local pH changes resulting from the water electrolysis have caused release of the analyte 128 from the capture species 126, the capture species 126 may remain adhered to the surface 124, as shown in the far right hand pane of FIG. 2. Due to the transient nature of the local pH change resulting from water electrolysis, the pH may revert to that before the electrolytic regeneration. The binding sites of the capture species 126 may thus be restored and may remain fully functional for binding further analyte 128.

Thus, the water electrolysis-based regeneration of the surface 124 may be achieved in a manner which is electrically and biologically safe, and avoids excessive power consumption. The surface 124 may therefore be regularly regenerated, thereby to enhance the life-time and reusability of the sensor unit 104, while retaining a suitably high measurement sensitivity for the analyte 128. Moreover, the requirement for a reagent, e.g. an elution buffer, to regenerate the surface 124 may be minimized or removed.

The formation of gases (H$_2$, O$_2$ or Cl$_2$, etc.) during electrolysis (see Equations 1 and 2) may not preclude detection of the bound analyte 128 with sufficient accuracy and reliability. The gases, and H$_2$ in particular, may be absorbed in the aqueous medium. For example, the gases may be dissolved in the sweat, in the case of sweat monitoring. Alternatively, the gases, and H$_2$ in particular, may form 'nanobubbles' which do not or only minimally impact the detection. The absorbed gas bubbles or nanobubbles may be too small to interfere with microfluidic flow within the device 101.

Moreover, a delay may be employed between regeneration and subsequent detection to permit any small quantity of gas to dissolve before detection. Alternatively or additionally, electrolysis gases may be released via the gas vent 148, and/or via channels or holes in the sensor unit 104. In a non-limiting example, such gases may be released from the sensor unit 104 via the apertures of a hydrophobic mesh. Once the gases have escaped from the surface 124, any interference of such gases on detection of the bound analyte 128 may be avoided.

Figure 3:
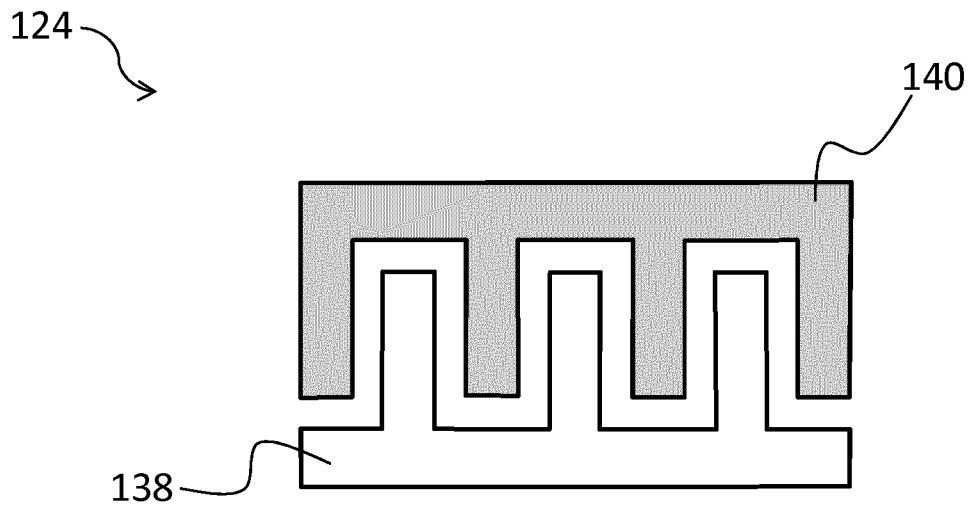
FIG. 3 shows interdigitated electrically conductive areas according to an embodiment.

FIG. 3 shows interdigitated electrically conductive areas 134 according to an embodiment. FIG. 3 shows a plan view of the surface 124; the capture species 126 (not shown in FIG. 3) being oriented normal to the surface 124. When the power supply 136 provides the D.C. voltage across the electrically conductive areas 134, one of the respective conductive areas 134 becomes the anode 138 and the other of the respective conductive areas 134 becomes the cathode 140, as previously described in relation to FIG. 2.

Figure 4:
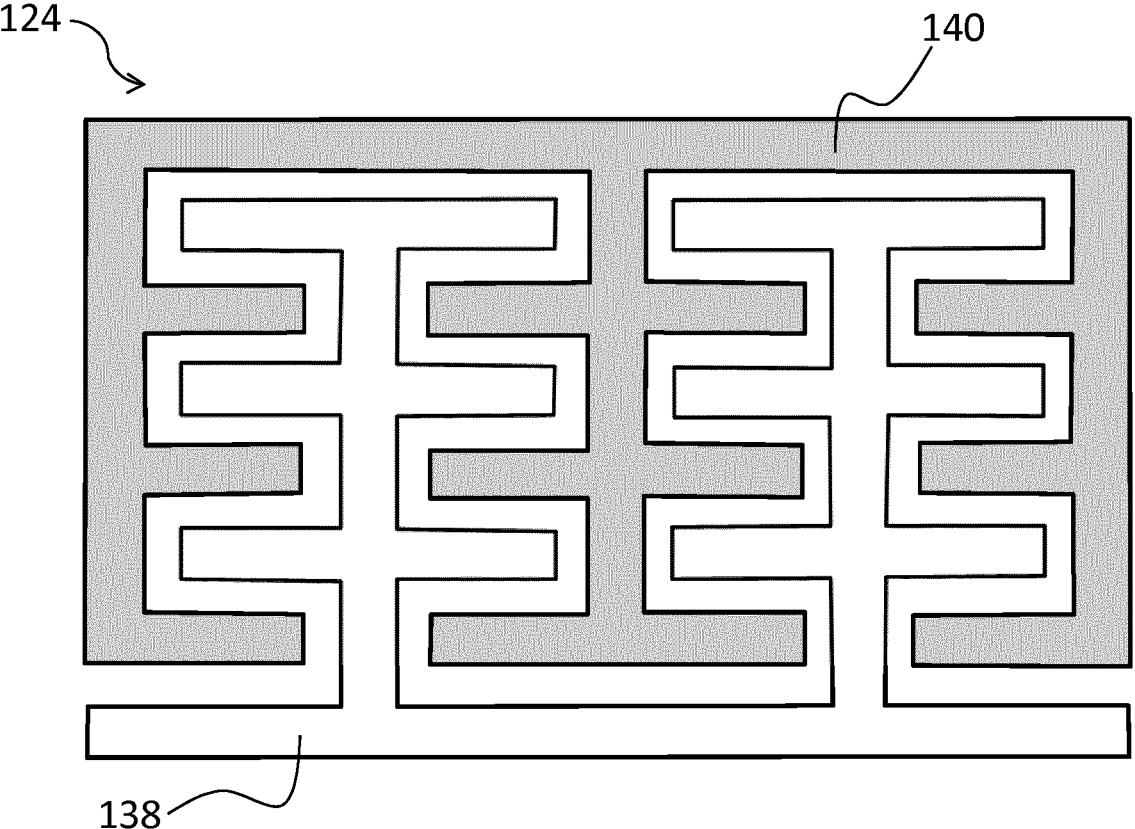
FIG. 4 shows interdigitated electrically conductive areas according to another embodiment.

FIG. 4 shows interdigitated electrically conductive areas 134 according to another embodiment. In this case, multiple interdigitated portions are provided on the surface 124. The comb-like interdigitated electrodes 138, 140 shown in FIGS. 3 and 4 may assist to provide the voltage over a relatively large area, e.g. in the order of several cm$^2$, whilst providing localities on the surface 124 in which the local pH changes resulting from water electrolysis drive regeneration of the surface 124 by disrupting the binding kinetics of the capture species 126-analyte 128 complex, as previously described in relation to FIG. 2.

A similar effect may be achieved using, for instance, electrically conductive areas 134 arranged as a plurality of concentric ring-like portions. Such an arrangement may facilitate the dual use of the electrically conductive areas 134 in respective sensing and regeneration modes, e.g. as electrodes of a quartz crystal resonator detector 130 in the sensing mode, as previously described.

Figure 5:
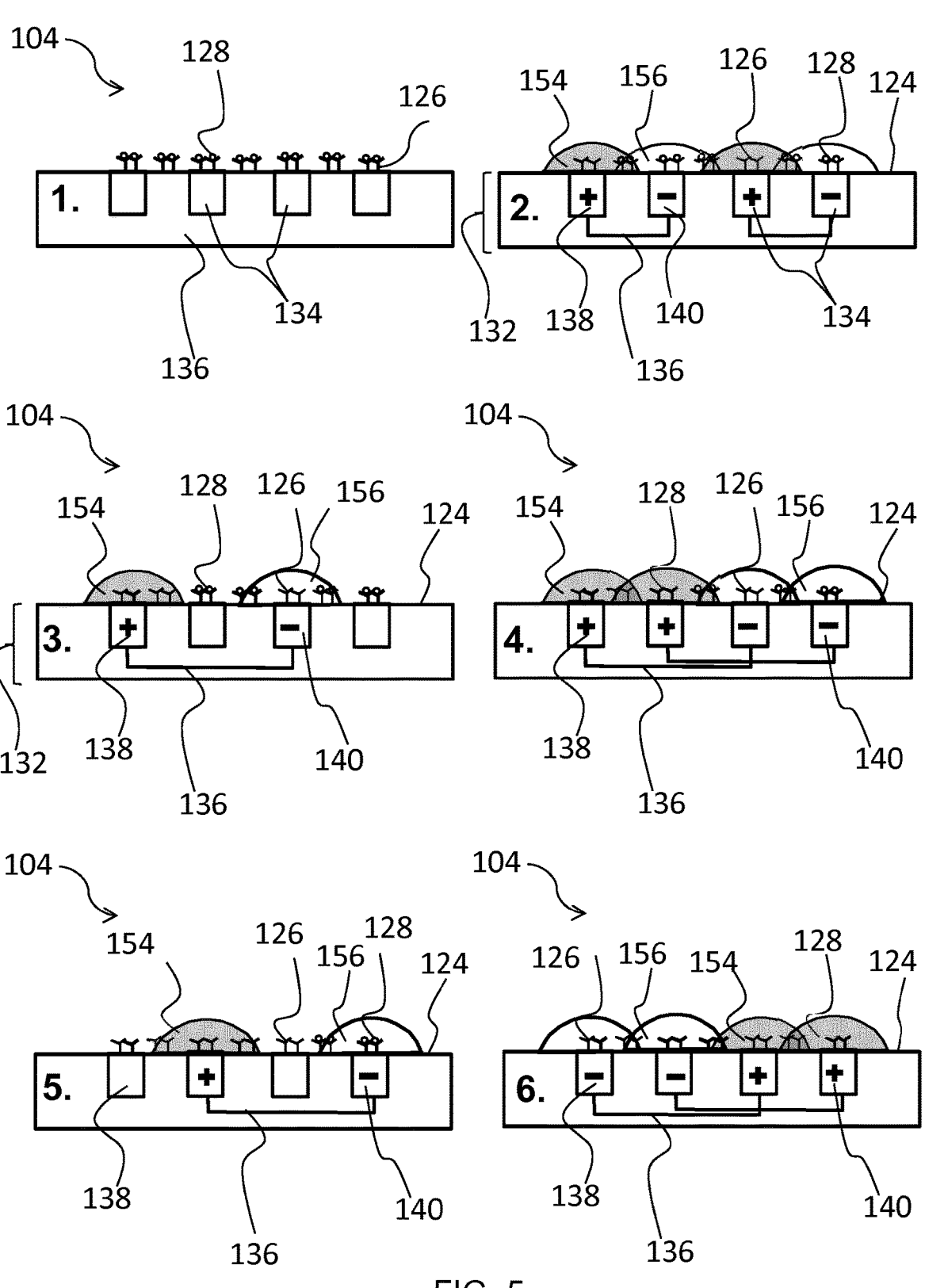
FIG. 5 shows settings of an electrolysis assembly according to an embodiment.
Figure 6:
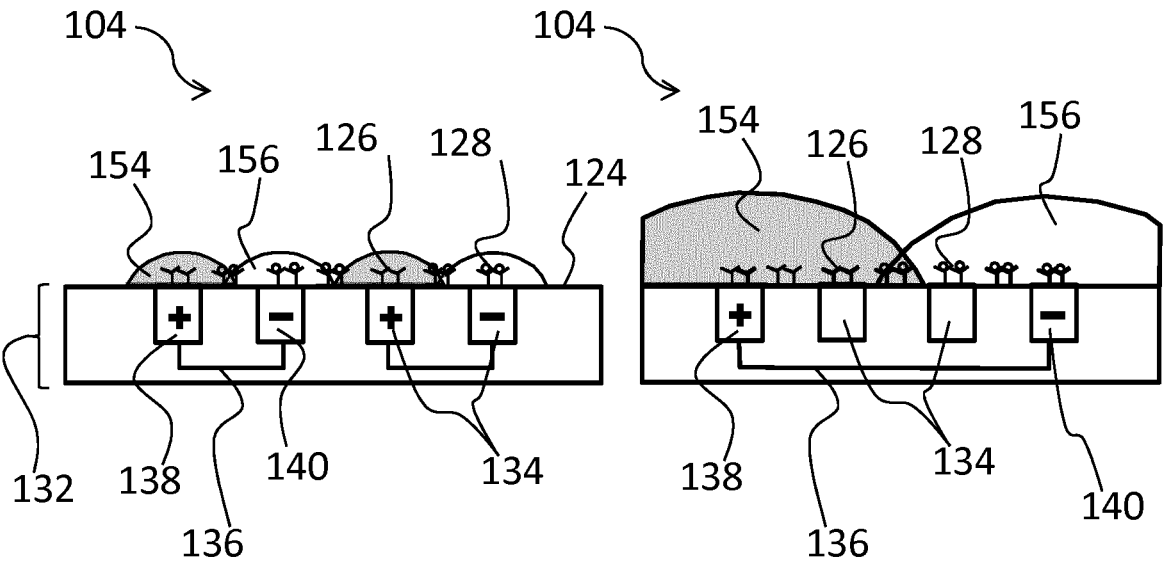
FIG. 6 shows two settings of an electrolysis assembly according to another embodiment.

In the embodiments shown in FIGS. 5 and 6, the electrically conductive areas 134 may be optically transmissive, thereby to enable label-free detection of the analyte 128, as previously described. In other non-limiting examples, non-optically transmissive materials, such as gold, may be employed for the electrically conductive areas 134.

In an embodiment, the plurality of spatially separated electrically conductive areas 134 comprises at least three conductive areas 134, and the power supply 136 is configured to implement at least a first setting and a second setting. In the first setting, the voltage is generated across a first pairwise combination of the at least three conductive areas 134. In the second setting, the voltage is applied across a second pairwise combination of the at least three conductive areas 134. The second pairwise combination is different from the first pairwise combination.

The power supply 136 may, for example, include a suitable switch arrangement for switching between the respective settings. The switch arrangement may be controlled manually by the user and/or may be operated automatically, e.g. via the controller 142.

When the voltage is provided across the respective electrodes 138, 140, a pH neutral zone may be present therebetween in which the analyte 128 remains bound to the capture species 126. By the power supply 136 being configured to implement the first setting and the second setting, the effective area of the surface 124 which is not exposed to a sufficiently low (or high) pH to effect regeneration may be reduced. If different settings are applied sequentially, the surface can be completely regenerated.

The capability of the power supply 136 to implement the first and second settings may be of particular assistance when, for example, the electrically conductive areas 134 cannot be made of optically transmissive materials. When a detection principle is employed which requires optical interrogation of the surface, such as surface plasmon resonance, electrically conductive areas 134 which are insufficiently optically transmissive may mean that only regions therebetween may be used for analyte sensing. Also the thickness of the layer may play a role. With the case of surface plasmon resonance, an evanescent field penetrates into the liquid with an exponential decrease of light intensity, and thus the generated signal is lower further away from the surface, e.g. when a transparent layer is atop the surface. However, capture species 126 located between the electrically conductive areas 134 may be more likely to coincide with a pH neutral zone during regeneration if only a single setting were employed; little or no regeneration occurring in such a pH neutral zone. The first and second settings may mean that a greater proportion of the capture species 126 located between the conductive areas 134 may be regenerated.

Such sequential activation of the electrically conductive areas 134 may thus shift the pH neutral zone, thereby to enable a greater proportion of the surface 124 to be regenerated, e.g. than if only a single setting were used.

FIG. 5 shows the reference setting before electrolysis (top left figure), and five different settings of an electrolysis assembly 132 according to an embodiment. FIG. 5 provides cross-sectional views through the capture surface 124 in order to schematically illustrate the settings. The first setting is shown on the top right hand side of FIG. 5. In this non-limiting example, the local acidic pH at the anodes 138 causes the analyte 128 to be liberated from the capture species 126. The patterned areas 154 denote positive charge (ion) clouds corresponding to localities having the acidic pH. The localities having the alkaline pH, denoted by the unpatterned areas 156 corresponding to negative charge (ion) clouds, proximal to the cathodes 140 may not, in this example, result in the analyte 128 being released from the capture species 126. Moreover, regeneration may not occur at the pH neutral areas between, and particularly midway between, the respective electrodes 138, 140.

Various second settings (used alone or successively) are shown in the middle and bottom row of FIG. 5. The respective electrodes 138, 140 in the second setting may be spaced further from each other than the respective electrodes 138, 140 in the first setting. In the second setting, capture species 126 which previously remained complexed to the analyte 128 in the first setting may be regenerated, because the positioning of the pH neutral zone is different in the second setting than in the first setting. When used in a sequential order, the various settings—which in this particular example all have in common the use of an equal electrolysis voltage—will lead to a sequential regeneration of capture surface.

FIG. 6 shows first and second settings which are similar to those shown in the FIG. 5 except that a higher voltage across the respective electrodes (conductive areas) 138, 140 is employed in the second setting (on the right hand side of FIG. 6) than in the first setting (on the left hand side of FIG. 6). As schematically depicted in FIG. 6, in contrast to FIG. 5 where an equal voltage was used in the respective settings, the higher voltage in the second setting may extend the positive charge cloud 154, i.e. relative to the positive charge clouds 154 evident in the first setting, such that further capture species 126 are regenerated upon switching to the second setting.

In an embodiment, the electrically conductive areas 134 may comprise an array of conductive areas 134 in which the spacing between adjacent conductive areas 134 alternates between a larger and a smaller separation. This embodiment is schematically depicted in FIG. 7.

Figure 7:
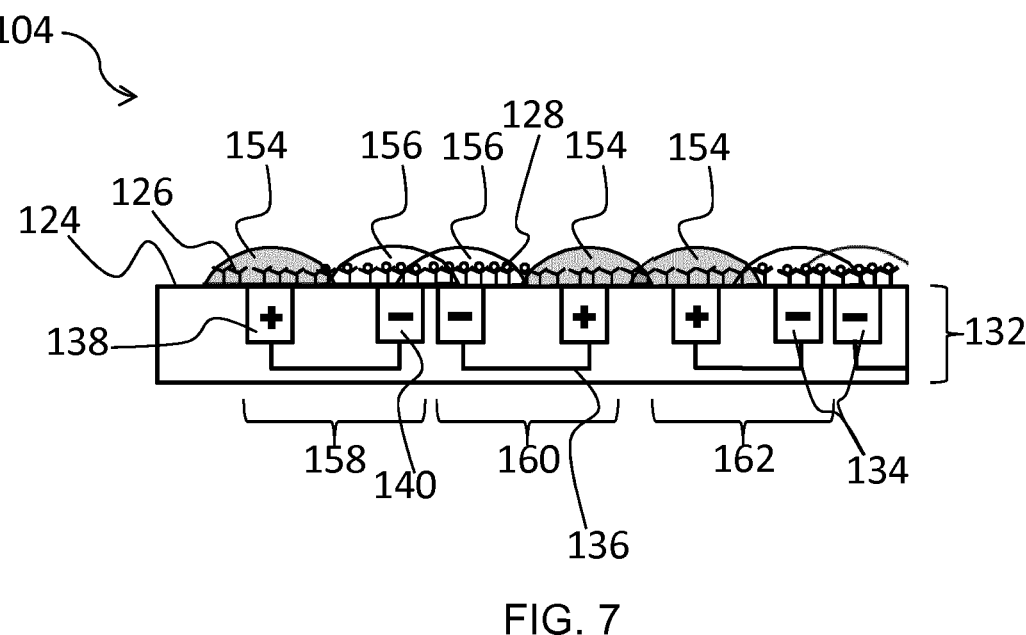
FIG. 7 shows a setting of an electrolysis assembly according to still another embodiment.

The power supply 136 may be configured to supply the voltage across adjacent conductive areas 134 spaced by the larger separation, such as to form the pairs of electrodes 158, 160 and 162 shown in FIG. 7. Moreover, adjacent conductive areas 134 which are spaced by the smaller separation may be of the same polarity as each other. Such an arrangement may assist to minimize the charge cloud 156 associated with the more closely spaced adjacent conductive areas 134, which may assist to reduce the area in which electrolytic regeneration may not occur. Accordingly, such an asymmetric electrode arrangement with relatively wide spaces between electrodes of the same or opposite polarity may enhance the efficiency with which the surface 124 is regenerated.

In the example shown in FIG. 7, adjacent conductive areas 134 which are spaced by the smaller separation correspond to cathodes 140; the analyte 128 not being liberated from the capture species 126 at the alkaline pH local to the cathodes 140. On the other hand, the more widely spaced anodes 138 may result in a relatively broad acidic locality (ion cloud 154) in which the analyte 128 is freed from the capture species 126.

It is noted that more widely spaced cathodes 140 (and thus more narrowly spaced anodes 138) may, for example, provide a similar effect for liberating the analyte 128 from capture species 126 when dissociation at an alkaline pH, i.e. at the cathodes 140, is favoured over dissociation at an acidic pH.

Figure 8:
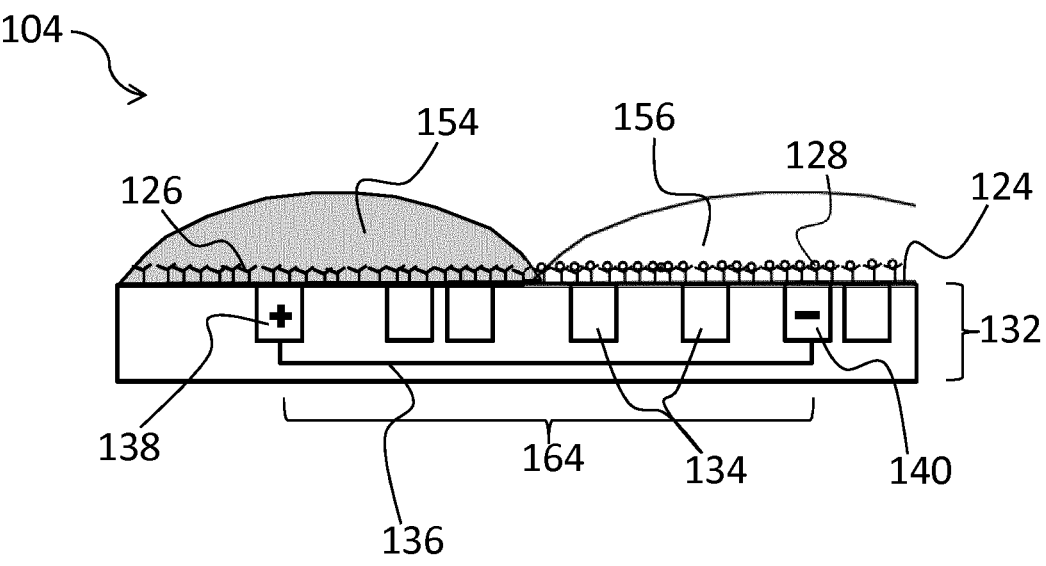
FIG. 8 shows a further setting of the electrolysis assembly shown in FIG. 7.

FIG. 8 shows a further setting of the electrolysis assembly 132 shown in FIG. 7. In FIG. 8, a voltage is applied across a further electrode pair 164 which are further apart from each other than any of the electrode pairs 158, 160, 162 in the setting shown in FIG. 7. Moreover, the voltage across the further electrode pair 164 in the further setting shown in FIG. 8 may be higher than that applied across the pairs of electrodes 158, 160, 162 in the setting shown in FIG. 7. This may enable a greater degree of regeneration of the surface 124, similarly to the scenario described previously in relation to FIG. 6.

In another embodiment, the electrically conductive areas 134 may be arranged as a grid of electrically conductive strips. A plan view of such a grid is schematically depicted in panes A), B) and C) of FIG. 9.

Figure 9:
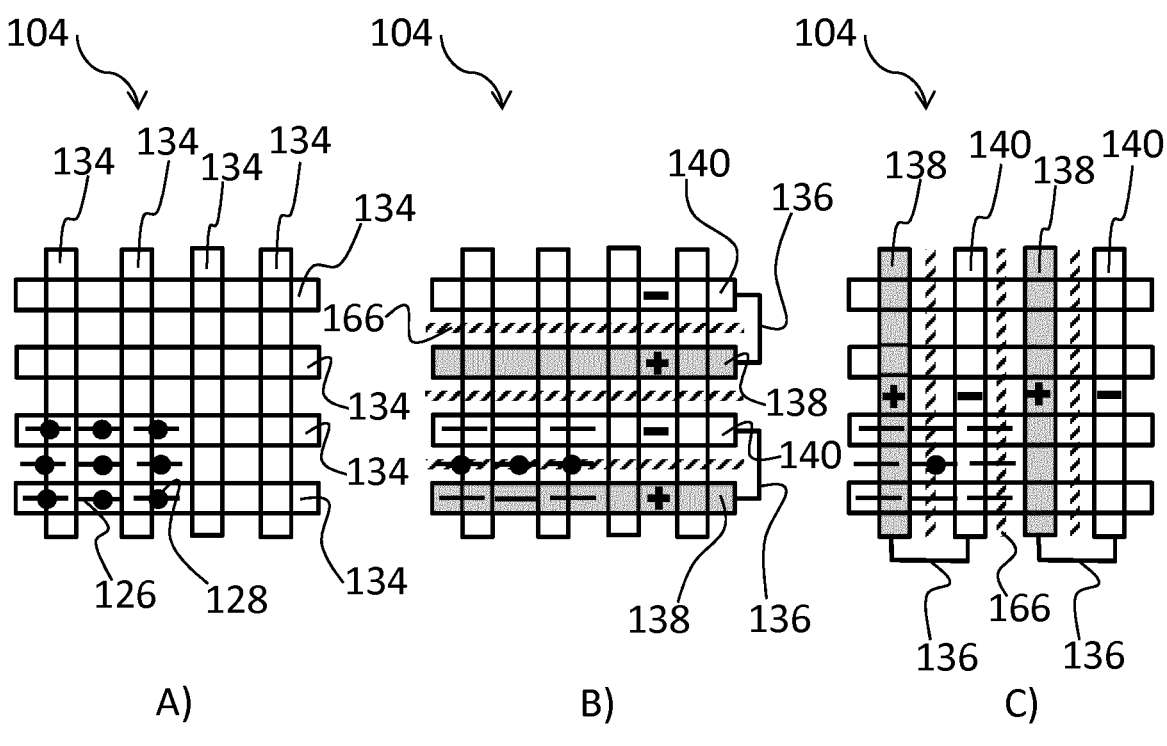
FIG. 9 shows modes of an electrolysis assembly according to a further embodiment.

Pane A) of FIG. 9 shows the sensor unit 104 prior to regeneration; the analyte 128 being bound to the capture species 126. Panes B) and C) of FIG. 9 schematically depict first and second modes respectively implemented by the power supply 136. In the first mode shown in pane B), the voltage is supplied across parallel strips 138, 140 extending in a first direction. In the scenario shown in FIG. 9, the analyte 128 is liberated from the capture species 126 at the local acidic pH of the anode 138 as well as at the local alkaline pH of the cathode 140, although acidic-only or alkaline-only regeneration may also be contemplated depending on the nature of the capture species 126 and the analyte 128.

Regeneration of the surface 124 does not, however, occur in the neutral regions 166 between each of the respective electrodes 138, 140. For this reason, and as shown in pane C) of FIG. 9, the power supply 136 is further configured to implement a second mode in which the voltage (of equal or different magnitude) is supplied across parallel strips extending in a second direction. The second direction is different from the first direction. For example, the first and second directions may be perpendicular to each other, as shown in the example of FIG. 9. The second mode may result in further regeneration of the surface 124.

Thus, almost complete regeneration of the surface 124 may be achieved by sequentially activating the electrically conductive areas 134, i.e. sequentially 'clocking through' electrode sub-segments of the grid.

Figure 10:
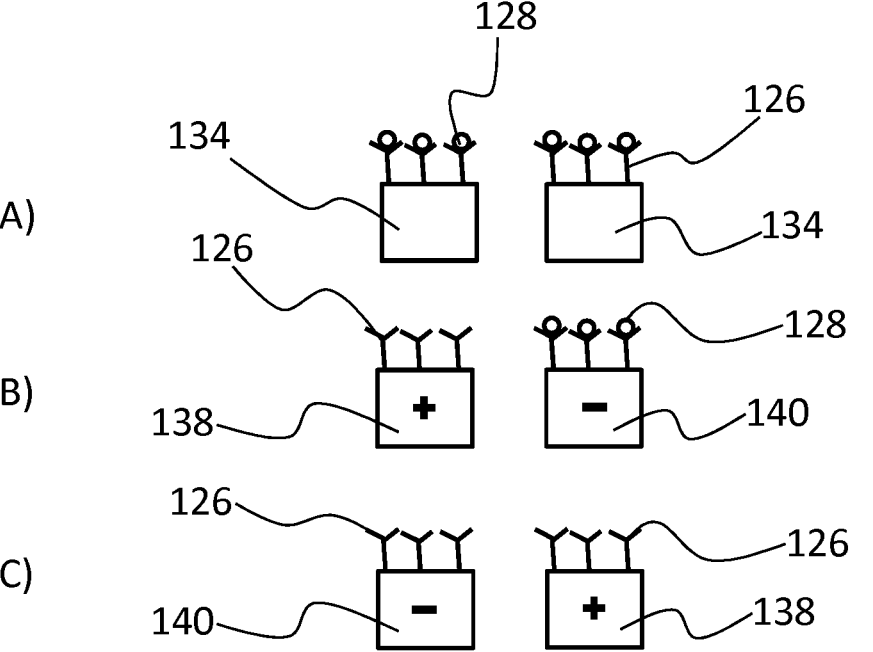
FIG. 10 shows regeneration of a capture surface of a sensor unit according to another embodiment.

In an embodiment, the power supply 136 may be configured to switch the polarity of the voltage across the at least two electrically conductive areas 134. FIG. 10 shows regeneration of a surface 124 of a sensor unit 104 comprising such a polarity switch. In A) of FIG. 10, the analyte 128 is bound to the capture species 126 prior to regeneration. In B) of FIG. 10, a voltage is supplied across the respective conductive areas 134, such as to provide an anode 138 and a cathode 140. The voltage in B) may be applied for a sufficient period of time, e.g. between 0.1 s and 10 s, to provide the local pH change necessary to cause dissociation of the analyte 128 from the capture species 126. However, in the scenario shown in FIG. 10, the surface 124 is only regenerated in the vicinity of one of the electrodes, in this case the anode 138. In this respect, certain antibody-antigen complexes, for instance, may be denatured only at an optimum acidic or alkaline pH, and are otherwise robust to large pH variations. For this reason, the power supply 136 may be configured to switch the polarity of the voltage across the respective electrically conductive areas 134, as shown in C) of FIG. 10. This polarity switch may result in regeneration of capture species 126 located proximal to both of the respective conductive areas 134.

Figure 11:
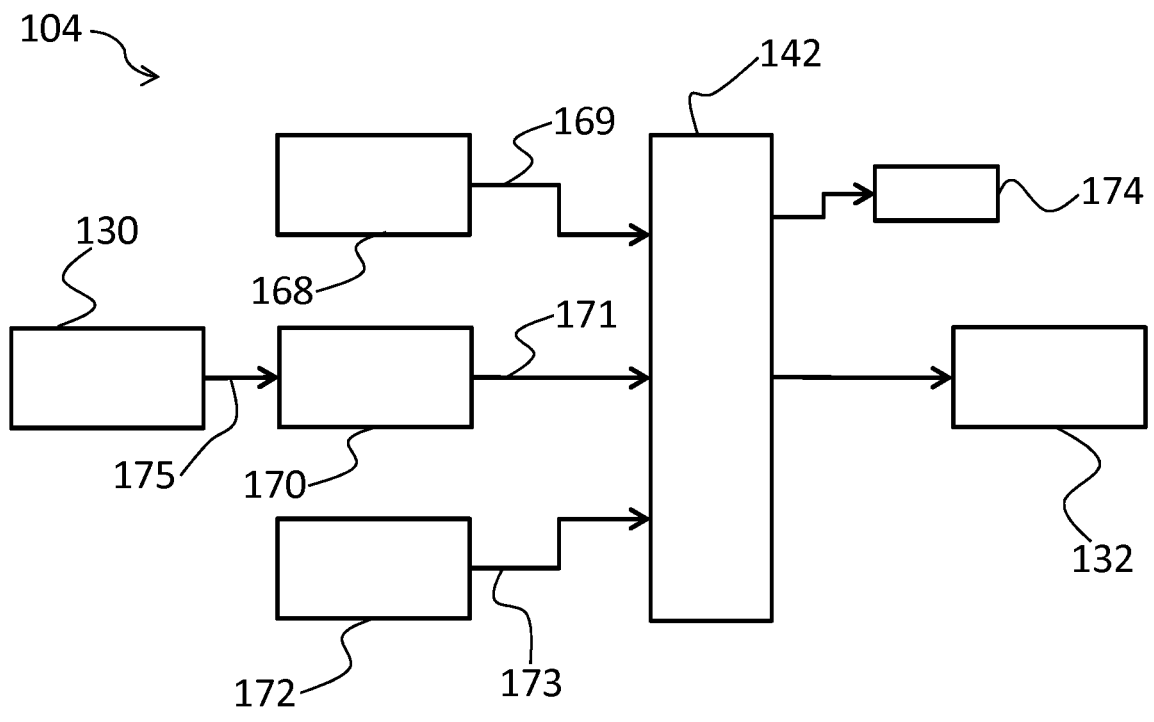
FIG. 11 shows a block diagram of a sensor unit according to an embodiment.

FIG. 11 shows a block diagram of a sensor unit 104 according to an embodiment. The sensor unit 104 comprises a controller 142 configured to trigger the electrolysis assembly 132 to electrolyse the aqueous medium. The arrow provided in FIG. 11 between the controller 142 and the electrolysis assembly 132 is intended to represent a control signal for triggering the power supply 136 of the electrolysis assembly 132 to regenerate the surface 124.

The sensor unit 104 may further comprise at least one of a clock module 168, a sensor signal variation module 170 and a further sensor 172.

The clock module 168 may be configured to send a clock signal 169 to the controller 142 at predetermined intervals, e.g. every one hour or every twelve hours. The controller 142 may trigger the electrolysis assembly 132 to regenerate the surface 124 in response to the clock signal 169. In this manner, periodic regeneration of the surface 124 may ensure consistent performance of the sensor unit 104.

The sensor signal variation module 170 may be configured to generate a variation signal 171 in response to a signal 175 received from the detector 130. The controller 142 may trigger the electrolysis assembly 132 to regenerate the surface 124 in response to the variation signal 171. Regeneration of the surface 124 may therefore be triggered in response to a change in the signal 175 due to analyte-capture species binding received from the detector 130.

In a non-limiting example, regeneration of the surface 124 may be triggered when the signal 175 received from the detector 130 is indicative of saturation of the detector 130. The binding of the analyte 128 to the capture species 126 may, for example, follow the Langmuir kinetic model for binding, and thus binding may follow a linear adsorption curve followed by a deviating part which is indicative of saturation. The variation signal 171 may, for instance, be triggered when the signal 175 indicates that the detector 130 is saturated or is above a predetermined threshold. By triggering regeneration when the detector 130 becomes saturated, a constant measurement when the detector 130 is in the linear adsorption regime may be ensured, such as to attain more accurate and reliable sensing performance.

In a non-limiting example, the variation signal 171 may additionally cause the controller 142 to trigger an acoustic and/or optical alarm 174, in order to alert the user that sensor performance has deteriorated, e.g. due to contamination or biofouling. If the regeneration of the surface 124 does not cause cessation of the alarm 174, the user may be alerted that the sensor unit 104 should be replaced.

The sensor unit 104 may comprise a further sensor 172 for monitoring a body parameter. For example, the further sensor 172 may monitor at least one of the heart rate, respiration rate, core body temperature and electrocardiogram of the patient. An event signal 173 may be produced by the further sensor 172 in response to a physiological event, such as a rise or drop in heart rate/respiration rate, a rise in core body temperature or an abnormal electrocardiogram. The event signal 173 may trigger regeneration of the surface 124. The sensor unit 104 may thus be prepared for analyte sensing when the physiological condition of the subject indicates that such analyte sensing would be of diagnostic use.

More generally, triggering electrolytic regeneration of the surface 124 in response to a suitable signal 169, 171, 173 may be advantageous in terms of enabling long-term automatic monitoring of the subject. When the power supply 136 comprises a cell or battery, such control over the electrolysis assembly 132 may assist to conserve cell- or battery-life.

Figure 12:
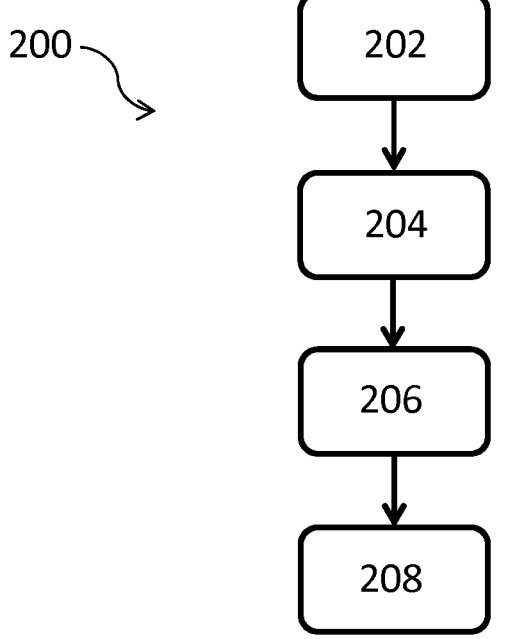
FIG. 12 shows a flowchart of a method according to an embodiment.

FIG. 12 shows a flowchart of a method 200 according to an embodiment. The method 200 is for detecting an analyte in an aqueous medium, e.g. sweat, saliva, tear fluid, etc. In step 202, a surface on which capture species are immobilized is provided. The surface and the capture species may be, for instance, the surface 124 and the capture species 126 described above in relation to FIGS. 1-11.

In step 204, the aqueous medium is received on the surface, thereby to permit the analyte to bind to the capture species. The bound analyte is detected in step 206, e.g. using the detector 130 described above in relation to FIG. 1.

Following detection, the analyte is released from the capture species in step 208 by electrolysing the water of the aqueous medium received on the surface. Electrolysis of water generates acidic and alkaline localities of the surface which may cause the analyte to dissociate from the capture species, as previously described. The electrolysis may, for example, be effected using the electrolysis assembly 132 of any of the embodiments described above.

The present invention may be applied in the long-term monitoring of biofluid/biomarkers in portable or wearable sampling devices 101 attached to the skin 107. On demand regeneration of the sensor unit 104 may facilitate monitoring of, for instance, high risk patients, such as those with serious chronic conditions, those in post-operative recovery, and the elderly.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A sensor unit for detecting an analyte in an aqueous medium, the sensor unit comprising:
   a surface for receiving the aqueous medium thereon;
   capture species for reversibly binding said analyte, the capture species being immobilized on the surface;
   a detector for detecting, determining or assessing analyte bound to the capture species; and
   an electrolysis assembly including:
   at least three spatially separated electrically conductive areas, all disposed on the same surface on which the capture species are immobilized and which receives the aqueous medium; and
   a power supply configured to implement:
   a first setting in which a first voltage sufficient to electrolyse the aqueous medium received on the surface is supplied across a first pairwise combination of the at least three spatially separated electrically conductive areas; and
   a second setting in which a second voltage sufficient to electrolyse the aqueous medium received on the surface is supplied across a second pairwise combination of the at least three spatially separated electrically conductive areas, the second pairwise combination being different from the first pairwise combination.

2. The sensor unit according to claim 1, wherein at least two of the at least three spatially separated electrically conductive areas are arranged relative to each other in an interdigitated configuration.

3. The sensor unit according to claim 1, wherein at least one of a magnitude and polarity of the second voltage supplied in the second setting is different from at least one of a magnitude and polarity of the first voltage supplied in the first setting.

4. The sensor unit according to claim 1, wherein the second pairwise combination of the at least three spatially separated electrically conductive areas are spaced further apart on the surface than the first pairwise combination of the at least three spatially separated electrically conductive areas.

5. The sensor unit according to claim 1, wherein the at least three spatially separated electrically conductive areas includes an array of conductive areas in which the spacing between adjacent conductive areas alternates between a larger separation and a smaller separation; and wherein said power supply is configured to supply the first voltage and the second voltage across adjacent conductive areas spaced by the larger separation, the adjacent conductive areas spaced by the smaller separation being of the same polarity as each other.

6. The sensor unit according to claim 1, wherein the at least three spatially separated electrically conductive areas include a grid of electrically conductive strips, the power supply being configured to implement: a first mode in which the first voltage sufficient to electrolyse the aqueous medium is supplied across parallel strips extending in a first direction; and a second mode in which the second voltage sufficient to electrolyse the aqueous medium is supplied across parallel strips extending in a second direction, the second direction being different from the first direction.

7. The sensor unit of claim 6, wherein the power supply is further configured to sequentially implement the first mode and the second mode.

8. The sensor unit according to claim 6, wherein the transducer includes at least one of a quartz crystal resonator detector and a surface plasmon detector.

9. The sensor unit according to claim 1, wherein the power supply is configured to switch a polarity of the first voltage across the at least three spatially separated electrically conductive areas.

10. The sensor unit according to claim 1, wherein the detector includes a transducer.

11. The sensor unit according to claim 10, wherein the transducer is arranged to transmit and/or receive electrical signals via at least one of the at least three spatially separated electrically conductive areas.

12. The sensor unit according to claim 1, wherein the at least three spatially separated electrically conductive areas include an optically transmissive material.

13. The sensor unit according to claim 1, further comprising: a controller configured to trigger the electrolysis assembly to electrolyse the aqueous medium in response to a trigger signal.

14. The sensor unit according to claim 13, wherein the controller includes a sensor signal variation module configured to generate a variation signal in response to a signal received from the detector, the trigger signal including the variation signal.

15. The sensor unit according to claim 13, further comprising: a further sensor for monitoring a body parameter, the further sensor being configured to generate an event signal in response to a change in said body parameter, wherein the trigger signal includes said event signal.

16. The sensor unit according to claim 13, wherein the controller includes a clock module configured to send a clock signal to the controller at predetermined intervals, the trigger signal including the clock signal.

17. The sensor unit according to claim 14, wherein the signal variation module is configured to generate the variation signal in response to saturation of the detector.

18. A body fluid monitoring device for detecting an analyte in an aqueous medium produced by a body, the body fluid monitoring device comprising: the sensor unit according to claim 1; and a fluid collection assembly for supplying the aqueous medium to the surface of the sensor unit.

19. The body fluid monitoring device of claim 18, wherein the body fluid monitoring device is a sweat monitoring device.

20. A method for detecting an analyte in an aqueous medium, the method comprising:

providing capture species immobilized on a surface;

receiving the aqueous medium on the surface such that the analyte binds to the capture species;

detecting, determining or assessing the analyte bound to the capture species; and subsequent to detecting, determining or assessing the analyte bound to the capture species, releasing the analyte from the capture species by electrolysing the aqueous medium received on the surface, wherein the electrolysing includes:

supplying a first voltage sufficient to electrolyse the aqueous medium across a first pairwise combination of at least three spatially separated electrically conductive areas, all disposed on the same surface on which the capture species are immobilized and which receives the aqueous medium, and supplying a second voltage sufficient to electrolyse the aqueous medium across a second pairwise combination of the at least three spatially separated electrically conductive areas, the second pairwise combination being different from the first pairwise combination.

* * * * *